(12) United States Patent
Suhadolnik et al.

(10) Patent No.: US 6,586,519 B1
(45) Date of Patent: Jul. 1, 2003

(54) THIOETHER SUBSTITUTED HYDROXYBENZOPHENONES AND STABILIZED COMPOSITIONS

(75) Inventors: Joseph Suhadolnik, Yorktown Heights, NY (US); Carmen Hendricks, White Plains, NY (US); Roger Meuwly, Cournillens (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 08/451,109

(22) Filed: May 25, 1995

Related U.S. Application Data

(62) Division of application No. 08/221,137, filed on Mar. 31, 1994.

(51) Int. Cl.[7] ............................................. C08L 31/04
(52) U.S. Cl. ...................................................... 524/509
(58) Field of Search ......................................... 524/509

(56) References Cited

U.S. PATENT DOCUMENTS

| | | | |
|---|---|---|---|
| 2,983,708 A | | 5/1961 | Lappin |
| 3,399,237 A | * | 8/1968 | Dressler et al. ............... 568/43 |
| 3,431,306 A | * | 3/1969 | Head et al. .................... 568/43 |
| 3,649,695 A | | 3/1972 | Millonis |
| 4,029,684 A | | 6/1977 | Avar et al. |
| 4,051,161 A | | 9/1977 | Proskow |
| 4,278,804 A | | 7/1981 | Ashby et al. |
| 4,297,513 A | | 10/1981 | Felder et al. |
| 4,824,892 A | | 4/1989 | Eiglmeier et al. |
| 4,911,732 A | | 3/1990 | Neumann et al. |

FOREIGN PATENT DOCUMENTS

| | | |
|---|---|---|
| DE | 3315281 | 11/1991 |
| EP | 0309909 | 4/1989 |
| EP | 0446740 | 9/1991 |
| GB | 2120264 | 11/1983 |

OTHER PUBLICATIONS

Plastics Additive Handbook, pp. 176–179, (1993).*
Modern Plastics Encyclopedia, pp. 174–177, (1983).*
Ueda et al., Synthesis Aromatic Poly(Thioether Ketone), (1992) 5. Poly Sci, Part A; Polychem, v.30, pp. 1993–1998.
McGraw–Hill, Modern Plastics Encyclopedia Oct. 1983, v. 60, No. 10–4 pp. 174–177.
Gachter et al. Plastics Add. Handbook pp. 176–179 (1993).
G.W. Klump. Reactivity in Organic Chemistry J. Wiley & Sons 1983, New York pp. 103, 105&106.

* cited by examiner

*Primary Examiner*—Samuel Barts
(74) *Attorney, Agent, or Firm*—Luther A. R. Hall; Tyler A. Stevenson

(57) ABSTRACT

2-Hydroxybenzophenone derivatives substituted in the 4'-position by a thioether moiety exhibit enhanced absorption in the UV at longer wavelength. Compositions comprising organic material subject to actinic degradation are beneficially stabilized with such derivatives.

18 Claims, No Drawings

THIOETHER SUBSTITUTED HYDROXYBENZOPHENONES AND STABILIZED COMPOSITIONS

This is a divisional of Ser. No. 08/221,137, filed Mar. 31, 1994.

This invention relates to 2-hydroxybenzophenone derivatives substituted in the 4'-position by a thioether moiety which exhibit enhanced UV absorption and to stabilized compositions containing said compounds.

BACKGROUND OF THE INVENTION

The use of various types of UV absorbers in the stabilization of polymers is well known. These stabilizers function by absorbing incident UV radiation and dissipating the absorbed energy in a non-destructive manner. The spectral region of greatest importance ranges from about 280 nm, the onset of solar radiation, through about 400 nm at which point absorbance imparts color to the system. Obviously, to be effective for general use, a compound should have a strong absorbance over a significant portion of this spectral region.

o-Hydroxybenzophenones have a long history of use as UV absorbers, but they suffer, however, from limited absorbance at the longer UV wavelengths.

Quite surprisingly, it is found that substitution of o-hydroxybenzophenones with a thioether at the 4'-position, i.e. on the non-hydroxy bearing ring, overcomes this shortcoming by significantly enhancing the longer wavelength absorption. This enhancement is particularly surprising since closely related 4'-sulfonyl substituted o-hydroxybenzophenones, some of which are previously disclosed, do not show this notable enhancement.

Examples of sulfur substitution on hydroxybenzophenones are known. Sulfonate groups have been added to either the hydroxy bearing or non-hydroxy bearing ring to improve water miscibility. There is no noted effect on UV absorption.

Thioether substitution on the hydroxy bearing ring of a benzophenone is known. U.S. Pat. No. 3,399,237 describes the preparation of 6,6'-thio-bis(4-benzoylresorcinol), in essence a sulfur-linked dimer of 2,4-dihydroxybenzophenone. This derivative has a broader range of UV absorption than the parent benzophenone. The sulfonyl and sulfonyl analogues have also been disclosed in U.S. Pat. No. 3,649,695, but no mention is made of any effect by this substituent on UV absorption.

Sulfonyl substitution on the non-hydroxy bearing ring is known. Various 4'-ethylsulfonyl-2-hydroxybenzophenones are found in U.S. Pat. No. 3,431,306. An example of a 4'-phenylsulfonyl derivative is found in U.S. Pat. No. 4,029,684. No change in absorbance due to this sulfonyl substitution is reported.

The generic description of the compounds provided by U.S. Pat. No. 4,029,684 describes an innumerable host of derivatives which would include some of the compounds of the instant invention. However, no thioether derivatives are actually prepared. The closest example is the previously mentioned, 4'-phenylsulfonyl derivative which fails to exhibit any of the enhanced UV absorbance of the corresponding instant 4'-phenylthio derivative.

Thus, the existing prior art anticipates neither the strong effect of thioether substitution on the non-hydroxy bearing ring of a benzophenone, nor the differences between a 4'-thioether substituent and a 4'-sulfonyl substituent on the nature of the UV absorption.

The present invention offers an improvement over the existing prior art compounds in that it provides a class of hydroxybenzophenone derivatives which absorb strongly over a broader range of UV wavelengths. It should be further noted that not only is the range of absorption increased, but that the intensity of absorption is also increased over much of this range. This increase in intensity is significant enough to result in stronger absorbance on a per weight basis despite the higher molecular weight of the instant compounds.

DETAILED DISCLOSURE

The instant invention pertains to compounds of formula I

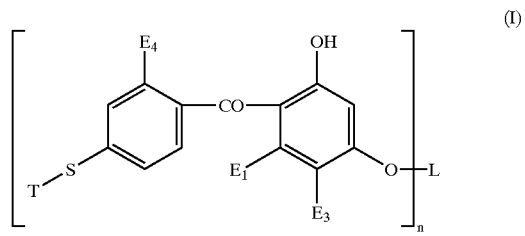

wherein n is 1 to 4,

T is alkyl of 1 to 20 carbon atoms, alkyl of 2 to 12 carbon atoms substituted by hydroxyl, by alkoxy of 1 to 12 carbon atoms, by siloxysilyl group of formula IV, by alkanoyloxy of 2 to 12 carbon atoms, by alkenoyloxy of 3 to 12 carbon atoms or by halogen, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, $E_1$ is hydrogen or —$OE_2$, $E_2$ is hydrogen or alkyl of 1 to 18 carbon atoms, $E_3$ is hydrogen or alkyl of 1 to 8 carbon atoms, $E_4$ is hydrogen or hydroxyl, when n is 1, L is hydrogen, straight or branched chain alkyl of 1 to 20 carbon atoms, said alkyl substituted by alkoxycarbonyl of 2 to 20 carbon atoms, by carboxyl, by alkylcarbonyl of 2 to 20 carbon atoms, by alkenylcarbonyl of 3 to 18 carbon atoms, or by siloxysilyl group of formula IV, alkyl of 2 to 20 carbon atoms substituted by one or two hydroxyl, by alkoxy of 1 to 12 carbon atoms or by phenoxy, alkyl of 2 to 20 carbon atoms substituted by one hydroxyl and by alkoxy of 1 to 12 carbon atoms or by phenoxy, or alkyl of 2 to 20 carbon atoms substituted by alkanoyloxy of 2 to 20 carbon atoms or by alkenoyloxy of 3 to 20 carbon atoms, glycidyl, alkyl of 4 to 20 carbon atoms interrupted by one to six oxygen atoms, by one or two carbonyloxy or oxycarbonyl groups, or L is alkanoyl of 2 to 18 carbon atoms, alkenoyl of 3 to 18 carbon atoms, benzoyl, benzoyl substituted by one or two alkyl of 1 to 4 carbon atoms or a group of formula II or III

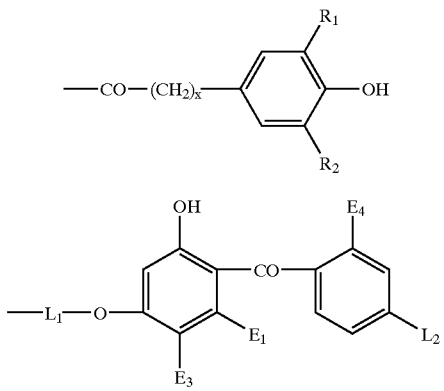

(II)

(III)

where
x is 0, 1 or 2,
$R_1$ is alkyl of 1 to 12 carbon atoms or cycloalkyl of 5 to 8 carbon atoms,
$R_2$ is sec- or tert-alkyl of 3 to 12 carbon atoms or cycloalkyl of 5 to 8 carbon atoms,
$L_1$ has the same meaning as L when n is 2,
$L_2$ is hydrogen or alkyl of 1 to 18 carbon atoms,
when n is 2, L is straight or branched chain alkylene of 1 to 12 carbon atoms, alkylene of 3 to 12 carbon atoms substituted by hydroxyl, by alkoxy of 1 to 8 carbon atoms, by alkoxycarbonyl of 2 to 20 carbon atoms, by alkanoyloxy of 2 to 20 carbon atoms, by alkenoyloxy of 3 to 20 carbon atoms or by a siloxysilyl group of formula IV, or L is alkylene of 4 to 20 carbon atoms interrupted by one or two carbonyloxy or oxycarbonyl groups, alkylene of 4 to 20 carbon atoms interrupted by one to six oxygen atoms, o-xylylene, m-xylylene, p-xylylene, isophthaloyl, phthaloyl, terephthaloyl or a,ɯ-alkanedioyl of 4 to 12 carbon atoms,
when n is 3, L is straight or branched chain alkanetriyl of 3 to 12 carbon atoms, alkanetrioyl of 3 to 12 carbon atoms, trimellitoyl or alkanetriyl of 6 to 20 carbon atoms interrupted by three carbonyloxy or oxycarbonyl groups,
when n is 4, L is straight or branched chain alkanetetrayl of 4 to 16 carbon atoms, alkanetetroyl of 4 to 16 carbon atoms, pyromellitoyl or alkanetetrayl of 8 to 24 carbon atoms interrupted by four carbonyloxy or oxycarbonyl groups, and
where, when T or L is a group of formula IV,

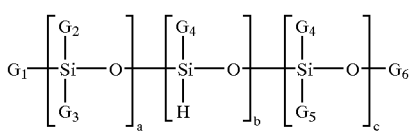

(IV)

where
a is 1–50,
b is 0–50,
c is 0–50,
$G_1$ is hydroxyl, alkyl of 1 to 12 carbon atoms, alkoxy of 1 to 4 carbon atoms, cyclohexyl or —O—Si$(G_4)_3$,
$G_2$ is $G_4$ or —O—Si$(G_4)_3$,
$G_3$ is a direct bond or a bivalent group of the formula —$CH_{2n}$—, —$(CH_2)_nO$—, —$CH_2CH(OH)CH_2O$— or —$CH_2CH(OH)CH_2$—O—$(CH_2)_3$— where n is 1 to 4,
$G_4$ is alkyl of 1 to 12 carbon atoms, alkoxy of 1 to 4 carbon atoms, cyclohexyl or phenyl,
$G_5$ is alkyl of 1 to 18 carbon atoms, alkoxy of 1 to 4 carbon atoms, cycloalkyl of 5 to 7 carbon atoms or phenyl, and
$G_6$ is hydrogen, alkyl of 1 to 12 carbon atoms, cyclohexyl, phenyl or —Si$(G_4)_3$, or $G_1$ and $G_6$ are linked together to form a direct bond.

Preferably, n is 1 or 2, most preferably 1.

Preferably, T is alkyl of 1 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms.

Most preferably, T is alkyl of 1 to 18 carbon atoms, allyl, cyclohexyl, phenylalkyl of 7 to 9 carbon atoms, phenyl or said phenyl substituted by one or two methyl groups. Especially preferably, T is alkyl of 4 to 12 carbon atoms or phenyl.

Preferably $E_1$ is hydrogen or is —$OE_2$ where $E_2$ is hydrogen or alkyl of 1 to 12 carbon atoms; most preferably where $E_2$ is hydrogen or alkyl of 1 to 8 carbon atoms.

Preferably $E_3$ is hydrogen.

Preferably $E_4$ is hydrogen or hydroxyl.

Preferably, when n is 1, L is hydrogen, alkyl of 1 to 12 carbon atoms, alkyl of 2 to 12 carbon atoms substituted by alkoxycarbonyl of 2 to 12 carbon atoms, by alkanoyloxy of 2 to 12 carbon atoms or by alkenoyloxy of 3 to 12 carbon atoms, alkyl of 2 to 4 carbon atoms substituted by hydroxyl, alkyl of 2 to 4 carbon atoms substituted by alkoxy of 2 to 8 carbon atoms or by phenoxy, alkyl of 2 to 4 carbon atoms substituted by one hydroxyl and by alkoxy of 2 to 8 carbon atoms or phenoxy, alkanoyl of 2 to 8 carbon atoms, or L is a group of formula II where x is 0 and $R_1$ and $R_2$ are each tert-alkyl of 4 to 8 carbon atoms or a group of formula IV.

Most preferably, when n is 1, L is hydrogen, alkyl of 3 to 8 carbon atoms, said alkyl substituted by alkoxycarbonyl of 2 to 8 carbon atoms, by alkanoyloxy of 2 to 8 carbon atoms or by alkenoyloxy of 3 to 8 carbon atoms, or L is 2-hydroxyethyl, alkyl of 3 carbon atoms substituted by alkoxy of 2 to 8 carbon atoms or by phenoxy, alkyl of 3 carbon atoms substituted by one hydroxyl and by alkoxy of 2 to 8 carbon atoms or phenoxy, alkanoyl of 2 to 4 carbon atoms or a group of formula II where x is 0 and $R_1$ and $R_2$ are each tert-butyl.

Preferably, when n is 2, L is alkylene of 3 to 12 carbon atoms, said alkylene substituted by hydroxy or interrupted by carbonyloxy or oxycarbonyl.

Most preferably, when n is 2, L is alkylene of 3 to 10 carbon atoms.

The thioethers of the instant invention are prepared by reacting equivalent amounts of a thiol or the alkali salt of a thiol with an appropriate derivative of 4-chloro-2-hydroxybenzophenone in the presence of an alkali base. The product of this reaction can be further derivatized to the appropriate final product.

The intermediate compounds needed to prepare the instant compounds are largely items of commerce or can be easily made by methods known in the art.

When L is alkyl substituted by OH or by alkoxy and/or interrupted by —O—, L is, for example, methoxyethyl, ethoxyethyl, butoxyethyl, butoxypropyl, $CH_3OCH_2CH_2OCH_2CH_2$—, $CH_3CH_2OCH_2CH_2OCH_2CH_2$—, $C_4H_9OCH_2CH_2OCH_2CH_2$—, dodecyloxypropyl 2-hydroxyethyl, 2-hydroxypropyl, 4-hydroxybutyl, 6-hydroxyhexyl, 2-hydroxyethyl, 2-hydroxypropyl, —CH$_2$CHOHCH$_2$O-alkyl or —CH$_2$CHOHCH$_2$O-phenyl.

When any of T, L, R$_1$, R$_2$, E$_2$ or E$_3$ is alkyl, such groups are, for example, methyl, ethyl, isopropyl, n-butyl, isobutyl, sec-butyl, tert-butyl, tert-amyl, 2-ethylhexyl, tert-octyl, lauryl, tert-dodecyl, tridecyl, n-hexadecyl, n-octadecyl and eicosyl; when any of said radicals is alkenyl, such groups are, for example, allyl or oleyl; when any of said radicals is cycloalkyl, such groups are, for example, cyclopentyl, cyclohexyl, cycloheptyl, cyclooctyl and cyclododecyl; when any of said radicals are phenylalkyl, such groups are, for example, benzyl, phenethyl, α-methylbenzyl and α,α-dimethylbenzyl; and when any of said radicals is aryl, they are, for example, phenyl, naphthyl, or when substituted by alkyl are, for example, tolyl and xylyl.

When L is alkylene, it is, for example, ethylene, tetramethylene, hexamethylene, 2-methyl-1,4-tetramethylene, 2,2-dimethyl-1,3-trimethylene, hexamethylene, octamethylene, decamethylene and dodecamethylene.

When L is alkanoyl, it is, for example, acetyl, propionyl, butyryl, capryl or lauroyl.

When L is alkanetriyl, it is, for example, 1,2,3-propanetriyl, 1,2,2-neopentanetriyl or 1,2,2-neohexanetriyl.

When L is alkanetetryl, it is, for example, pentaerythrityl or 1,2,3,4-butanetetrayl.

When L is a group substituted by alkanoyloxy, such a group is acetoxy or butyryloxy. When L is a group substituted by alkenoyloxy, such a group is acryloyloxy or methacryloyloxy.

This invention also relates to the use of the instant compounds as intermediates useful in the preparation of other red-shifted UV absorbing compounds. For example, EP O 446 740 A2 details the preparation of unsymmetric bis-benzophenones through the ester forming reaction of a hydroxyalkyl benzophenone with a dissimilarly substituted carboxyalkyl benzophenone. Unsymmetric compounds containing the instantly substituted benzophenones are included in this invention.

Other examples of difunctional and polyfunctional benzophenone derivatives prepared via simple esterification reactions of existing benzophenones are found in U.S. Pat. Nos. 4,911,732 and 2,983,708. Difunctional and polyfunctional thio-substituted benzophenones are exemplified in the instant invention.

Also known is the conversion of benzophenone derivatives to polymerizable and copolymerizable compounds through simple derivation. For example, U.S. Pat. No. 4,824,892 discloses a benzophenone methacrylate prepared via acylation of an existing benzophenone UVA. There also exist a host of disclosures such as DE 33 15 281 C2 and U.S Pat. Nos. 4,278,804 and 4,051,161 describing the conversion of benzophenone UVAs to silyl or siloxy derivatives which can be polymerized or polymer bound during use. The use of the instant compounds in the preparation of such polymerizable species is exemplified in this invention as well.

The instant compounds can be used to stabilize any number of organic substrates. Particular emphasis is placed on resins which are more susceptible to UV light of longer wavelengths such as polyphenylene sulfide and epoxide coatings systems. However, the instant compounds are not limited to compositions of thermoplastic resins such as polypropylene, polyethylene, polyesters, polyvinyl chloride, polyurethanes, polyamides, polyphenylene sulfide, polyphenylene oxide, polystyrene, polyacrylates, polyacetal, rubbers such as polybutadiene, copolymers and blends such as styrene and acrylonitrile on polybutadiene, and resin systems used in coatings applications such as acrylic resins with melamine cross-linking agents, acrylic alkyd or polyester resins with isocyanate cross-linking agents and epoxide resins with carboxylic acid, anhydride or amine cross-linking agents.

The instant invention also pertains to a composition stabilized against actinic induced degradation which comprises (a) an organic material subject to actinic induced degradation, and (b) an effective stabilizing amount of a compound of formula I.

In general polymers which can be stabilized include

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, Vib or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/ailyl acrylate copolymers, ethylene/altyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrenefisoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichloro hydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer, polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aninocarboxylic acids or the corresponding lactams, for example polyamide 4, polyamide 6, polyamide 6/6, 6/10, 6/9, 6/12, 4/6, 12/12, polyamide 11, polyamride 12, aromatic polyamides starting from m-xylene diamine and adipic acid; polyamides prepared from hexamethylenediamine and isophthalic or/and terephthalic acid and with or without an elastomer as modifier, for example poly-2,4,4-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-imethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.
31. Polysiloxanes such as the soft, hydrophilic polysiloxanes described, for example, in U.S. Pat. No. 4,259,467; and the hard polyorganosiloxanes described, for example, in U.S. Pat. No. 4,355,147.
32. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
33. Radiation curable compositions containing ethylenically unsaturated monomers or oligomers and a polyunsaturated aliphatic oligomer.
34. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.05 to about 3%, and especially 0.05 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. ANTIOXIDANTS 1.1. Alkylated Monophenols, for Example
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol
1.2. Alkylated Hydroguinones, for Example
2,6-di-tert-butyl-4-methoxyphenol
2,5-di-tert-butyl-hydroquinone
2,5-di-tert-amyl-hydroquinone
2,6-diphenyl-4-octadecyloxyphenol
1.3. Hydroxylated Thiodiphenyl Ethers, for Example
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)
1.4. Alkylidene-bisphenols, for Example
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.
1.5. Benzyl Compounds, for Example
1,3,5-tri-(3,5-di-tert-butyl-4-hydroxybenzyl)-2,4,6-trimethylbenzene
di-(3,5-di-tert-butyl-4-hydroxybenzyl)sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for Example
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-Butyl-4-hydroxyphenyl)-propionic Acid With Monohydric or Polyhydric Alcohols, for Example

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-Butyl-4-hydroxy-3-methylphenyl)-propionic Acid With Monohydric or Polyhydric Alcohols, for Example

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-Butyl-4-hydroxyphenyl)-propionic Acid for Example
N,N'-di-(3,5-di-tert-butyl-4-hydroxyphenylpropionyl)-hexamethylenediamine
N,N'-di-(3,5-di-tert-butyl-4-hydroxyphenylpropionyl)-trirethylenediamine
N,N'-di-(3,5-di-tert-butyl-4-hydroxyphenylpropionyl)-hydrazine 1.10 Diarylamines, for Example
diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV ABSORBERS AND LIGHT STABILIZERS 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, dodecylated-5'-methyl derivatives, and difunctional compounds such as 2,2'-methylene-bis[4-methyl-6-(benzotriazol-2-yl)phenol].

2.2. 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl)sebacate, bis-(1,2,2,6,6-pentamethylpiperidyl)sebacate, n-butyl-3,5-di-tert.butyl-4-hydroxybenzyl malonic acid bis-(1,2,2,6,6-pentanemethylpiperidylkster, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1' (1,2-ethanediyl)-bis-(3,3,5,5-tetramethylpiperazinone), bis (1-octyloxy-2,2,6,6-tetramethylpiperidin-4-yl)sebacate.

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythritol diphosphite, tris-(2,4-di-tert-butylphenyl)phosphite, di-isodecylpentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyldithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

13. Benzofuranones and indolinones, for example those disclosed in U.S. Pat. No. 4,325,863, U.S. Pat. No. 4,338,244 or U.S. Pat. No. 5,175,312, or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The co-stabilizers, with the exception of the benzofuranones listed under 11, are added for example in concentrations of 0.01 to 10%, relative to the total weight of the material to be stabilized.

Further preferred compositions comprise, in addition to components (a) and (b) further additives, in particular phenolic antioxidants, light stabilizers or processing stabilizers.

Particularly preferred additives are phenolic antioxidants (item 1 of the list), sterically hindered amines (item 2.6 of the list), phosphites and phosphonites (item 4 of the list) and peroxide-destroying compounds (item 5.) of the list.

Additional additives (stabilizers) which are also particularly preferred are benzofuran-2-ones, such as described, for example, in U.S. Pat. No. 4,325,863, U.S. Pat. No. 4,338,244 or U.S. Pat. No. 5,175,312.

Examples of such benzofuran-2-ones are compounds of the formula

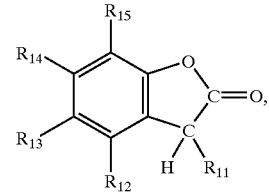

in which
$R_{11}$ is phenyl or phenyl which is substituted by 1 to 3 alkyl radicals together having at most 18 carbon atoms, alkoxy having 1 to 12 carbon atoms, alkoxycarbonyl having 2 to 18 carbon atoms or chlorine;

$R_{12}$ is hydrogen;

$R_{14}$ is hydrogen, alkyl having 1 to 12 carbon atoms, cyclopentyl, cyclohexyl or chlorine;

$R_{13}$ has the meaning of $R_{12}$ or $R_{14}$ or is a radical of the formula

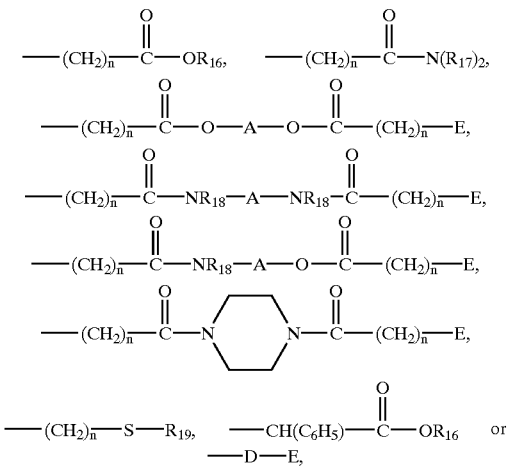

in which
$R_{16}$ is hydrogen, alkyl having 1 to 18 carbon atoms, alkyl having 2 to 18 carbon atoms which is interrupted by oxygen or sulfur, dialkylaminoalkyl having a total of 3 to 16 carbon atoms, cyclopentyl, cyclohexyl, phenyl or phenyl which is substituted by 1 to 3 alkyl radicals together having at most 18 carbon atoms;

n is 0, 1 or 2;

the substituents $R_{17}$, independently of one another, are hydrogen, alkyl having 1 to 18 carbon atoms, cyclopentyl, cyclohexyl, phenyl, phenyl which is substituted by 1 or 2 alkyl radicals together having at most 16 carbon atoms, a radical of the formula —$C_2H_4OH$,

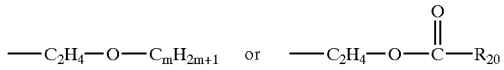

or together with the nitrogen atom to which they are attached form a piperidine or morpholine radical;

m is 1 to 18;

$R_{20}$ is hydrogen, alkyl having 1 to 22 carbon atoms or cycloalkyl having 5 to 12 carbon atoms;

A is alkylene having 2 to 22 carbon atoms which may be interrupted by nitrogen, oxygen or sulfur, $R_{18}$ is hydrogen, alkyl having 1 to 18 carbon atoms, cyclopentyl, cyclohexyl, phenyl, phenyl which is substituted by 1 or 2 alkyl radicals together having at most 16 carbon atoms, or is benzyl;

$R_{19}$ is alkyl having 1 to 18 carbon atoms;

D is —O—, —S—, —SO—, —SO$_2$— or —C(R$_{21}$)$_2$—;

the substituents $R_{21}$, independently of one another, are hydrogen, $C_1$–$C_{16}$alkyl, the two $R_{21}$ together containing 1 to 16 carbon atoms, $R_{21}$ is furthermore phenyl or a radical of the formula

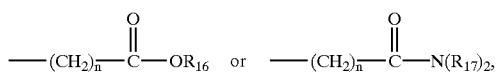

in which n, $R_{16}$ and $R_{17}$ are as defined above;

E is a radical of the formula

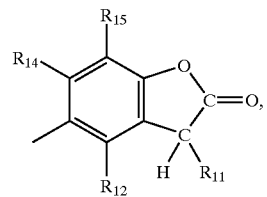

in which $R_{11}$, $R_{12}$ and $R_{14}$ are as defined above; and $R_{15}$ is hydrogen, alkyl having 1 to 20 carbon atoms, cyclopentyl, cyclohexyl, chlorine or a radical of the formula

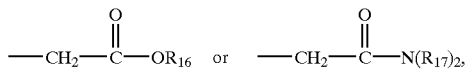

in which $R_{16}$ and $R_{17}$ are as defined above, or $R_{15}$ together with $R_{14}$ forms a tetramethylene radical.

Preference is given to those benzofuran-2-ones in which $R_{13}$ is hydrogen, alkyl having 1 to 12 carbon atoms, cyclopentyl, cyclohexyl, chlorine or a radical of the formula

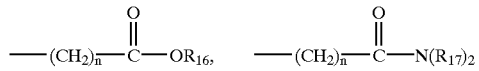

or —D—E, in which n, $R_{16}$, $R_{17}$, D and E are as defined above, $R_{16}$ is in particular hydrogen, alkyl having 1 to 18 carbon atoms, cyclopentyl or cyclohexyl.

Preference is given furthermore to those benzofuran-2-ones in which $R_{11}$ is phenyl or phenyl which is substituted by 1 or 2 alkyl radicals together having at most 12 carbon atoms; $R_{12}$ is hydrogen; $R_{14}$ is hydrogen or alkyl having 1 to 12 carbon atoms; $R_{13}$ is hydrogen, alkyl having 1 to 12 carbon atoms,

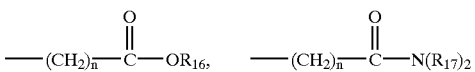

or —D—E; $R_{15}$ is hydrogen, alkyl having 1 to 20 carbon atoms,

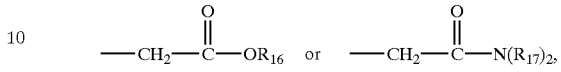

or $R_{15}$ together with $R_{14}$ forms a tetramethylene radical, n, $R_{16}$, $R_{17}$, D and E being as defined at the beginning.

Of particular interest are also those benzofuran-2-ones in which $R_{11}$ is phenyl; $R_{13}$ is hydrogen, alkyl having 1 to 12 carbon atoms or —D—E; $R_{12}$ and $R_{14}$, independently of one another, are hydrogen or alkyl having 1 to 4 carbon atoms; and $R_{15}$ is alkyl having 1 to 20 carbon atoms, D and E being as defined at the beginning.

Of special interest are finally also those benzofuran-2-ones in which $R_{11}$ is phenyl; $R_{13}$ is alkyl having 1 to 4 carbon atoms or —D—E; $R_{12}$ and $R_{14}$ are hydrogen; and $R_{15}$ is alkyl having 1 to 4 carbon atoms, cyclopentyl or cyclohexyl, D being a group —C(R$_{21}$)$_2$— and E being a radical of the formula

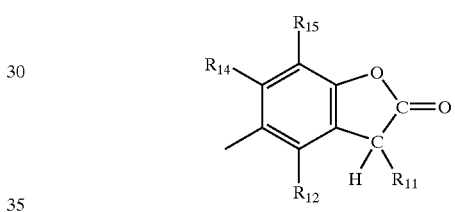

the substituents $R_{21}$, being identical to or different from one another and each being alkyl having 1 to 4 carbon atoms, and $R_{11}$, $R_{12}$, $R_{14}$ and $R_{15}$ being as defined.

The amount of additional additives, in particular stabilizers, for example of the benzo furan-2-ones mentioned, can vary within wide limits. For example, 0.0005 to 10, preferably 0.001 to 5, in particular 0.01 to 2, % by weight thereof can be present in the compositions according to the invention.

Incorporation of the alpha, monoclinic crystalline form of 2,2',2"-nitrilo[triethyl-tris-(3,3',5,5'-tetra-tert-butyl-1,1'-biphenyl-2,2'-diyl)phosphite] and, if desired, further additives in the polymer organic material is carried out by known methods, for example before or during moulding or by applying the dissolved or dispersed compounds to the polymer organic material, if appropriate with subsequent slow evaporation of the solvent. The alpha, monoclinicmodification according to the invention can also be added to the materials to be stabilized in the form of a masterbatch containing them, for example, in a concentration of 2.5 to 25% by weight.

The alpha, monoclinic modification according to the invention can also be added before or during polymerization or before crosslinking.

The alpha, monoclinic modification according to the invention can be incorporated in the material to be stabilized in pure form or encapsulated in waxes, oils or polymers.

The alpha, monoclinic modification according to the invention can also be sprayed onto the polymer to be stabilized. They are capable of diluting other additives (for example the abovementioned customary additives) or their melts, thus enabling them to be sprayed onto the polymer to be stabilized also together with these additives. Addition by spraying during deactivation of the polymerization catalysts is particularly advantageous, it being possible, for example, for the steam used for deactivation to be used for spraying.

In the case of bead polymerized polyolefins, it may be advantageous, for example, to apply the alpha, monoclinic modification according to the invention, if desired together with other additives, by spraying.

The materials thus stabilized can be used in a wide range of forms, for example as films, fibres, tapes, moulding compositions, profiles or as binders for paints, adhesives or cements.

As already mentioned, the organic materials to be protected are preferably organic, in particular synthetic, polymers. Of these, the materials being protected are particularly advantageously thermoplastic materials, in particular polyolefins. The excellent efficiency of the alpha, monoclinic-form of 2,2',2"-nitrilo[triethyl-tris-(3,3',5,5'-tetra-tert-butyl-1,1'-biphenyl-2,2'-diyl)phosphite] as processing stabilizer (thermal stabilizer) should be mentioned in particular. To this end, it is advantageously added to the polymer before or during its processing. It is however also possible to stabilize other polymers (for example elastomers) or lubricants or hydraulic fluids against degradation, for example light-induced or thermal-oxidative degradation. For elastomers, see the above list of possible organic materials.

Suitable lubricants and hydraulic fluids are based, for example, on mineral or synthetic oils or mixtures thereof. Lubricants are known to one skilled in the art and described in the relevant technical literature, for example in Dieter Klamann, "Schmierstoffe und verwandte Produkte" (Verlag Chemie, Weinheim 1982), in Schewe-Kobek, "Das Schmiermittel-Taschenbuch" (Dr. Alfred Hüthig-Verlag, Heidelberg, 1974) and in "Ullmanns Enzyklopädie der technischen Chemie" vol. 13, pages 85–94 (Verlag Chemie, Weinheim, 1977).

Accordingly, a preferred embodiment of the present invention is the process of using the alpha, monoclinic form of 2,2',2"-nitrilo[triethyl-tris-(3,3',5,5'-tetra-tert-butyl-1,1'-biphenyl-2,2'-diyl)phosphite] for stabilizing organic materials against oxidative, thermal or light-induced degradation.

The alpha, monoclinic modification according to the invention is preferably used as processing stabilizer (thermal stabilizer) of thermoplastic polymers.

The present invention also provides a process for stabilizing an organic material against oxidative, thermal or light-induced degradation, which comprises incorporating therein or applying thereto the alpha, monoclinic form of 2,2',2"-nitrilo[triethyl-tris-(3,3',5,5'-tetra-tert-butyl-1,1'-biphenyl-2,2'-diyl)phosphite].

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinnammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxycinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3-tris(2-methyl-4-hydroxy-5-tert-butylphenyl)butane, 1,3,5-tris[2-(3,5-di-tert-butyl-4-hydroxyhydrocinnamoyloxy) ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetraks(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl)sebacate, bis(1,2,2,6,6-pentamethylpiperidin-4-yl)sebacate, di(1,2,2,6,6-pentamethylpiperidin-4-yl)(3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl)nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2, 6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis-(amino-2,2,6,6-tetramethylpiperidine), N,N',N",N'"-tetrakis[(4,6-bis(butyl-2,2,6,6-tetramethyl-piperidin-4-yl)-amino-s-triazin-2-yl]-1, 10-diamino-4,7-diazadecane, mixed [2,2,6,6-tetramethylpipetidin-4-yl-β,β,β',β'-tetramethyl-3,9-(2,4,8, 10-tetraoxaspim[5.5]-undecane)diethyl]1,2,3,4-butanetetracarboxylate, mixed [1,2,2,6,6-pentamethylpiperidin-4-yl/β,β,β',β'-tetramethyl-3,9-(2,4,8, 10-tetraoxaspiro[5.5]undecane)diethyl]1,2,3,4-butanetetracarboxylate, octamethylene bis(2,2,6,6-tetramethylpiperidin-4-carboxylate), 4,4'-ethylenebis(2,2,6, 6-tetramethylpiperazin-3-one), and bis(1-octyloxy-2,2,6,6-tetramethylpiperidinyl)sebacate.

A most preferred hindered amine compound is bis(2,2,6, 6-tetramethylpiperidin-4-yl)sebacate, the polycondensation product of 1-(2-hydroxyethyl)-2,2,6,6-tetramethyl-4-hydroxypiperdine and succinic acid, the polycondensation product of 2,4-dichloro-6-tert-octylamino-s-triazine and 4,4'-hexamethylenebis(amino-2,2,6,6-tetramethylpiperidine), N,N ',N",N'"-tetrakis[(4,6-bis(butyl-(2,2,6,6-tetramethyl-piperidin-4-yl)amino)-s-triazine-2-yl]-1,0-diamino-4,7-diazadecane or especially bis(1-octyloxy-2,2,6,6-tetramethylpiperidin-4-yl)sebacate.

The lubricating oil may be a mineral oil, a synthetic oil or any mixture of such oils. Mineral oils are preferred and examples of these include paraffinic hydrocarbon oils e.g. a mineral oil having a viscosity of 46 $mm^2/s$ at 40° C.; "150

Solvent Neutral" a solvent refined neutral mineral oil having a viscosity of 32 mm²/s at 40° C.; and "solvent brightstocks", a high boiling residue from the process of refining mineral oil, and having a viscosity of 46 mm²/s at 400° C.

Synthetic lubricating oils which may be present may be synthetic hydrocarbons such as polybutenes, alkyl benzenes and poly-alpha olefins as well as simple di-, tri- and tetraesters, complex esters and polyesters derived from carboxylic acid esters of formula: $G_1$—OCC-alkylene-COO$G_2$ wherein "alkylene" denotes an alkylene residue having from 2 to 14 carbon atoms and $G_1$ and $G_2$ are the same or different and each is an alkyl group having from 6 to 18 carbon atoms. Tri-esters which are of use as lubricating oil base stocks are those derived from trimethylolpropane and $C_6$–$C_{18}$ monocarboxylic acids or mixtures thereof, whereas suitable tetraesters include those derived from pentaerythritol and a $C_6$–$C_{18}$ mono-carboxylic acid or mixtures thereof.

Complex esters suitable for use as components of the composition of the present invention are those derived from monobasic acids, dibasic acids and polyhydric alcohols, for instance the complex ester derived from trimethylol propane, caprylic acid and sebacic acid.

Suitable polyesters are those derived from any aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

Other lubricating oils are those known to the art-skilled and described e.g. in Schewe-Kobek, "Schmiermittel-Taschenbuch", (Huethig Verlag, Heidelberg 1974), and in D. Klamann, "Schmierstoff und verwandte Produkte", (Verlag Chemie, Weinheim 1982).

The lubricating oils applicational media can also contain other additives which may be added to improve the basic properties of lubricants e.g. metal passivators, viscosity-index improvers, pour-point depressants, dispersing agents, detergents, additional rust inhibitors, extreme pressure additives, anti-wear additives and antioxidants.

Examples of Phenolic Antioxidants

1. Alklated Monophenols 2,6-di-tert-butyl-4-methylphenol, 2,6-di-tert-butylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-i-butylphenol, 2,6-di-cyclopentyl-4-methylphenol, 2-(β-methylcyclohexyl)-4,6-dimethylphenol, 2,6-di-octa-decyl-4-methylphenol, 2,4,6-tri-cyclohexylphenol, 2,6-di-tert-butyl-4-methoxymethylphenol, o-tert-butylphenol.

2. Alkylated Hydroquinones 2,6-di-tert-butyl-4-methoxyphenol, 2,5-di-tert-butyl-hydroquinone, 2,5-di-tert-amyl-hydroquinone, 2,6-diphenyl-4-octa-decyloxyphenol.

3. Hydroxylated Thiodiphenylethers 2,2'-Thio-bis-(6-tert-butyl-4-methylphenol), 2,2'-thio-bis-(4-octyl-phenyl), 4,4'-thio-bis-(6-tert-butyl-3-methylphenol), 4,4'-thio-bis-(6-tert-butyl-2-methylphenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methyl-cyclohexyl)-phenol), 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5-isobutylphenol), 2,2'-methylene-bis-(6-(α-methylbenzyl-4-nonylphenol), 2,2'-methylene-bis-(6-(α,α-di-methylbenzyl)-4-nonylphenol), 4,4'-methylene-bis-(2,6-di-tert-butyl-phenol), 4,4'-methylene-bis-(6-tert-butyl-2-methylphenol), 1,1-bis-(5-tert-butyl-4-hydroxy-2-methyl-phenol)-butane, 2,6-di-(3-tert-butyl-5-methyl-2-hydroxybenzyl)-4-methyl-phenol, 1,1,3-tris-(5-tert-butyl-4-hydroxy-2-methylphenyl)-3-n-dodecyl)-mercaptobutane, ethyleneglycol-bis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5'-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-trimethyl-benzene, bis(3,5-di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethyl-benzyl)dithiolterephthalate, 1,3,5-tris-(3,5-di-tert-butyl-4-hydroxybenzyl)-isocyanurate, 1,3,5-tris-(4-tert-butyl-3-hydroxy-2,6-dimethylbenzyl)-isocyanurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acylaminophenols

4-Hydroxy-lauric acid anilide, 4-hydroxy-stearic acid anilide, 2,4-bis-octylmercapto-6-(3,5-di-tert-butyl-4-hydroxyanilino)-s-triazine, N-(3,5-di-tert-butyl-4-hydroxyphenyl)-carbamic acid octyl ester.

7. Esters of β-(3,5-di-tert-Butyl-4-hydroxyphenyl)-propionic Acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, bis-hydroxyethyl-oxalic acid diamide.

8. Esters of β-(5-tert-Butyl-4-hydroxy-3-methylphenyl)-propionic Acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate,thiodiethylene glycol, di-hydroxyethyl-oxalic acid diamide.

9. Amides of β-(3,5-di-tert-Butyl-4-hydroxyphenyl)-propionic Acid for example N,N'-Bis-(3,5Ai-tert-butyl-4-hydroxyphenylpropionyl)-hexamethylene-diamine, N,N'-bis-(3,5-di-tert-butyl-4-hydroxy-phenylpropionyl)-trimethylenediamine, N,N'-bis(3,5-di-tert-butyl-4-hydroxyphenylpropionyl)-hydrazine.

Examples of Amine Antioxidants

N,N'-di-isopropyl-p-phenylenediamine, N,N'-di-sec.-butyl-p-phenylenediamine, N,N'-bis(1,4-dimethyl-pentyl)-p-phenylenediamine, N,N'-bis(1-ethyl-3-methyl-pentyl)-p- phenylenediamine, N,N'-bis(1-methyl-heptyl)-p-phenylenediamine, N,N'-dicyclo-hexyl-p-phenylenediamine, N,N'-diphenyl-p-phenylenediamine, N,N'-di-(naphthyl-2)-p-phenylenediamine, N-isopropyl-N'-phenyl-p-phenylenediamine, N-(1,3-dimethyl-butyl)-N'-phenyl-p-phenylenediamine, N-(1-methyl-heptyl)-N'-phenyl-p-phenylene-diamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, di-phenylamine, N-allyldiphenylamine, 4-isopropoxydiphenylamine, N-phenyl-1-naphthylamine, N-phenyl-2-naphthylamine, octylated diphenylamine, e.g. p,p'-di-tert-octyldiphenylamine, 4-n-butylaminophenol, 4-butyrylamino-phenol, 4-nonanoylamino-phenol, 4-dodecanoyl-amino-phenol, 4-octadecanoyl-amino-phenol, di-(4-methoxy-phenyl)-amine, 2,6-di-tert-butyl-4-dimethyl-amino-methyl-phenol, 2,4'-diamino-diphenylmethane, 4,4'-diamino-diphenyl-methane, N,N,N',N'-tetramethyl-4,4'-diamino-diphenylmethane, 1,2-di-(phenyl-amino)-ethane, 1,2-di-[2-methyl-phenyl)-amino]-ethane, 1,3-di-(phenylamino)-propane, (o-tolyl)-biguanide, di-[4-1',3'-dimethyl-butyl)-phenyl]amine, tert-octylated N-phenyl-1-naphthylamine, mixture of mono- and dialkylated tert-butyl-/tert-octyldiphenylamines, 2,3-dihydro-3,3-dimethyl-4H-1,4-benzothiazine, phenothiazine, N-allylphenothiazine, tert-octylated phenothiazine, 3,7-di-tertoctylphenothiazine.

Examples for Other Antioxidants

Aliphatic or aromatic phosphites, esters of thiodipropionic acid or of thiodiacetic acid, or salts of dithiocarbamic or dithiophosphoric acid.

Examples of Metal Passivators, for Example for Copper, are

Triazoles, benzotriazoles and derivatives thereof, tolutriazole and derivatives thereof, e.g. di(2-ethylhexyl)-aminomethyltolutriazole, 2-mercaptobenzothiazole, 5,5'-methylene-bis-benzotriazole, 4,5,6,7-tetrahydrobenzotriazole, salicyclidene-propyleneiamine and salicyclamino-guanidine and salts thereof, 1,2,4-triazole and N,N'-disubstituted aminomethyl triazoles of formula

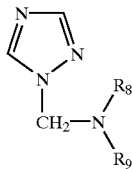

in which $R_8$ and $R_9$ are, independently, e.g. alkyl, alkenyl, or hydroxyethyl, obtained by reacting 1,2,4-triazole with formaldehyde and an amine, $HNR_8R_9$, as disclosed in European Patent Application No. 160620; and the Mannich reaction products derived from benzotriazole or tolutriazole, formaldehyde and an amine $HNR_8R_9$.

Examples of Rust Inhibitors are a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and amines, 4-nonyl-phenoxy-acetic acid.
b) Nitrogen-containing compounds, e.g. I. Primary, secondary or tertiary aliphatic or cycloaliphatic amines and amine-salts of organic and inorganic acids, e.g. oil-soluble alkyl-ammonium carboxylates II. Heterocyclic compounds, e.g. substituted imidazolines and oxazolines.
c) Phosphorus-containing compounds, e.g. amine salts of phosphonic acid or phosphoric acid partial esters, zinc dialkyldithio phosphates.
d) Sulfur-containing compounds, e.g. barium-dinonylnaphthalene-n-sulfonates, calcium petroleum sulfonates.
e) Derivatives of gamma-alkoxypropylamines described in Japanese Patent Publication No. 15783/1973; and
f) Salts having the formula $Y-NH_3-R_{10}CO_2-$ in which Y is a group $R_{11}X_1CH_2CH(OH)CH_2$ in which $R_{10}$ and $R_{11}$, independently, are e.g. alkyl and $X_1$ is O, $CO_2$, NH, N(alkyl), N(alkenyl) or S, these salts being prepared by mixing an amine $Y-NH_2$ with an acid $R_{10}CO_2H$, as disclosed in DE-OS 3437 876 (German Offenlegungsschrift).
g) Compounds having the formula $R_{12}-X_2-CH_2-CH(OH)-CH_2NR_{13}R_{14}$ in which $X_2$ is $-O-$, $-S-$, $-SO_2-C(O)-O-$ or $-N(Rd)$ in which $R_{12}$ is H or $C_1-C_{12}$alkyl, $R_{13}$ is unsubstituted $C_1-C_4$alkyl or $C_2-C_5$alkyl substituted by one to three hydroxyl groups, $R_{14}$ is hydrogen, unsubstituted $C_1-C_4$alkyl or $C_2-C_5$alkyl substituted by one to three hydroxyl groups provided that at least one of $R_{13}$ and $R_{14}$ is hydroxy-substituted, and $R_{12}$ is $C_2-C_{20}$alkyl $-CH_2-CH(OH)-CH_2NR_{13}R_{14}$ or $R_{12}$ is $C_2-C_{18}$alkenyl, $C_2-C_3$alkynyl or $C_5-C_{12}$ provided that, when $X_2$ is $-O-$ or $-C(O)-O-$, $R_{12}$ is branched $C_4-C_{20}$alkyl. These compounds are described in GB Patent Specification 2172284A.
h) Compounds having the formula:

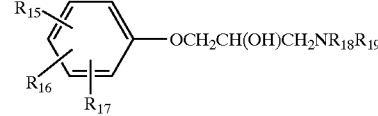

in which $R_{15}$, $R_{16}$, $R_{17}$ are, independently, hydrogen, $C_1-C_{15}$alkyl, $C_5-C_{12}$cycloalkyl, $C_6-C_{15}$aryl or $C_{7-C12}$aralkyl and $R_{18}$ and $R_{19}$, independently, are hydrogen, 2-hydroxyethyl or 2-hydroxypropyl, provided that $R_{18}$ and $R_{19}$ are not simultaneously hydrogen and, when $R_{18}$ and $R_{19}$ are each $-CH_2CH_2OH$, $R_{15}$ and $R_{16}$ are not simultaneously hydrogen and $R_{17}$ is not pentyl. These compounds are described in EP Patent specification 0 252 007.

Examples of Viscosity-index Improvers are

Polyacrylates, polymethacrylates, vinylpyrrolidone/methacrylate-copolymers, polyvinylpyrrolidones, polybutanes, olefin-copolymers, styrene/-acrylate-copolymers, polyethers.

Examples of Pour-point Depressants are

Polymethacrylates, alkylated naphthalene derivatives.

Examples of Dispersants/detergents are

Polybutenylsuccinic acid-amides or -imides, polybutenyl-phosphonic acid derivatives, basic magnesium-, calcium-, and bariumsulfonates and -phenolates.

Examples of Anti-wear Additives and Extreme Pressure Additives are

Sulphur- and/or phosphorus- and/or halogen-containing compounds e.g. sulphurised vegetable oils, zinc dialkyldithiophosphates, tritolylphosphate, chlorinated paraffins, alkyl- and aryldi- and trisulphides, triphenylphosphorothionate.

The compounds of the instant invention can be incorporated into polymer systems by any number of known methods. Their relatively high molecular weight make them particularly suited for applications where high processes temperatures are employed or where high concentrations near the surface are required, particularly as in the production of laminated articles as described in copending application Serial No. 08/029,211. The combination of high molecular weight and melting points near 100° C. make the instant compounds particularly useful in powder coating applications. Benzophenone derivatives have also seen wide use in dye bath applications, particularly for polyesters, and the instant compounds are also well suited for these applications.

The following examples are for illustrative purposes only and are not to be construed to limit the scope of the instant invention in any manner whatsoever.

EXAMPLE 1

4'-Phenylthio-2,4-dihydroxybenzophenone

To 50 grams of 4'-chloro-2,4-dihydroxybenzophenone and 27.8 grams of potassium carbonate in 50 mL of 1-methyl-2-pyrrolidinone (NMP) is added 22.2 grams of thiophenol. The resulting suspension is heated at 200° C. with strrring for 2.5 hours. The reaction mixture is then allowed to cool to room temperature, made acidic with 10% aqueous hydrochloric acid and extracted with ethyl acetate. The organic phase is washed with water and brine, dried over anhydrous magnesium sulfate and concentrated to leave 70 grams of a deep red syrup. The crude material is dissolved in an ethyl acetate/heptane mixture (1:1) and partially purified by filtration through a bed of silica gel to yield after concentration 66.6 grams of a light orange solid; $^1$H NMR and IR data are consistent with the tide compound; Mass. Spec m/z 322 (M$^+$).

EXAMPLE 2

4-Butoxy-2-hydroxy-4'-octylthiobenzophenone

Following the procedure of Example 1, 5.5 grams of 4'-chloro-2-hydroxy-4-butoxy-benzophenone is reacted with 2.6 grams of octanethiol and 2.5 grams of potassium carbonate in 20 mL of NMP to produce 7.3 grams of a light brown solid which is dissolved in ethyl acetate, filtered through a bed of silica gel and recrystallized to yield 2.1 grams of 4-butoxy-2-hydroxy-4'-tylthiobenzophenone as a pale yellow solid, melting at 77–79° C., Mass. Spec. m/z 414 (M$^+$).

Analysis: Calcd for $C_{25}H_{34}O_3S$: C, 72.4; H, 8.3; S, 7.7. Found: C, 71.6; H, 8.3; S, 7.9.

EXAMPLE 3

2-Hydroxy-4-octyloxy-4'-phenylthiobenzophenone

To a solution of 9.0 grams of 4'-phenylthio-2,4-dihydroxybenzophenone in 50 mL of N,N-dimethylformamide (DMF) is added 3.8 grams of potassium carbonate with stirring. 5.4 Grams of 1-bromooctane is added and the resulting mixture is heated near reflux for 1.5 hours. The reaction mixture is allowed to cool to room temperature, acidified with 10% aqueous hydrochloric acid and extracted with ethyl acetate. The organic layer is washed with water and brine, dried over anhydrous magnesium sulfate and concentrated to leave 9.7 grams of crude 2-hydroxy-4-octyloxy-4'-phenylthiobenzophenone which is purified by recrystallization from ethyl acetate/heptane to yield 2.8 grams of a near white solid, melting at 65–67° C., Mass Spec. m/z 434 (M$^+$).

Analysis: Calcd. for $C_{27}H_{30}O_3S$: C, 74.6; H, 7.0; S, 7.4. Found: C, 74.5; H, 6.8; S, 7.3.

EXAMPLE 4

Ethyl 6-[3-Hydroxy-4-(4-phenylthiobenzoyl) phenoxy]hexanoate

Following the procedure of Example 3, 5.0 grams of 4'-phenylthio-2,4-dihydroxybenzophenone, 2.1 grams of potassium carbonate and 3.5 grams of ethyl 6-bromohexanoate are reacted in 25 mL of DMF for 2.5 hours. Work-up provided 6.3 grams of a dark syrup which is purified by silica gel chromatography, heptane/ethyl acetate as eluent to yield 5.0 grams of ethyl 6-[3-hydroxy-4-(4-phenylthiobenzoyl)phenoxy]hexanoate as a yellow syrup, Mass. Spec. m/z 464 (M$^+$).

EXAMPLE 5

1,6-bis-[3-Hydroxy-4-(4-phenylthiobenzoyl) phenoxy]hexane

Following the procedure of Example 3, 15.0 grams of 4'-phenylthio-2,4-dihydroxybenzophenone, 6.4 grams of potassium carbonate and 5.7 grams of 1,6-dibromohexane are reacted in 100 mL of DMF for 1 hour. After work-up the resulting brown residue is dissolved in hot toluene, filtered through a bed of silica gel and concentrated to leave 13.3 grams of an orange syrup which is dissolved in ethyl acetate and triturated with heptane to yield 12.6 grams of 1,6-bis-[3-hydroxy-4-(4-phenylthiobenzoyl)phenoxy]hexane. Recrystallization from ethyl acetate/heptane yields 4 grams of a yellow solid, melting at 122–125° C., Mass. Spec. (ci, isobutane) m/z 727 (M$^+$+1).

EXAMPLE 6

1,10-bis-[3-Hydroxy-4-(4-phenylthiobenzoyl) phenoxy]decane

Following the procedure of Example 3, 5.0 grams of 4'-phenylthio-2,4-dihydroxybenzophenone, 2.1 grams of potassium carbonate and 1.9 grams of 1,10-dichlorodecane are reacted in 25 mL DMF for 1 hour. Aqueous work-up provided 6.9 grams of a brown solid which is dissolved in ethyl acetate and filtered through a bed of silica gel. The filtrate is partially concentrated and 2.1 grams of 1,10-bis [3-hydroxy-4-(4-phenylthiobenzoyl)phenoxy]-decane precipitates as light yellow crystals, melting at 125–127° C., Mass. Spec. (ci, isobutane) m/z 783 (M$^+$+1).

EXAMPLE 7

2-Hydroxy-4-(2-hydroxyethyloxy)-4'-phenylthiobenzophenone 5.0 Grams of 4'-phenylthio-2,4-dihydroxybenzophenone, 1.7 grams of ethylene carbonate and 1.4 grams of tetrabutylammonium iodide are heated together as a melt at 130° C. for 5 hours. The deep red reaction mixture is allowed to cool and water and ethyl acetate are added to the resulting syrup. The mixture is separated, the organic layer washed with water and brine, dried over anhydrous magnesium sulfate and concentrated leaving 5.5 grams of crude product which is purified by silica gel chromatography using ethyl acetate-:heptane 1:1 as eluent to yield 3.1 grams of 2-hydroxy-4-(2-hydroxyethyloxy)-4'-phenylthiobenzophenone as a near white solid, melting at 77–790° C., Mass. Spec. m/z 366 ($M^+$).

Analysis: Calcd for $C_{21}H_{18}O_4S$: C, 68.8; H, 4.9; S, 8.7. Found: C, 68.6; H, 4.6; S, 8.5.

EXAMPLE 8

2-Hydroxy-4-(2-hydroxy-3-phenoxypropoxy)-4'-phenylthiobenzophenone

To a solution of 4.0 grams of 4'-phenylthio-2,4-dihydroxybenzophenone and 1.9 grams of 1,2-epoxy-3-phenoxypropane (phenyl glycidyl ether) in 20 mL of DMF is added 0.2 grams of ethyl triphenylphosphonium iodide and the resulting mixture is heated to 140° C. with stirring for 5 hours. The reaction mixture is allowed to cool, made acidic with 10% aqueous hydrochloric acid and extracted with ethyl acetate. The organic layer is washed with water and brine, dried over anhydrous magnesium sulfate and concentrated. The residue is separated by silica gel chromatography using ethyl acetate/heptane 1:1 as eluent providing a fraction containing 2-hydroxy-4-(2-hydroxy-3-phenoxypropoxy)-4'-phenylthiobenzophenone which is further purified by recrystalization from ethyl acetate/heptane to yield 1.6 grams of a light orange solid, melting at 101–102° C., Mass. Spec. m/z 472 ($M^+$).

EXAMPLE 9

2-Hydroxy-4'-phenylthio-4-propionyloxybenzophenone

To a stirred solution of 5 grams of 4'-phenylthio-2,4-dihydroxybenzphenone and 2.2 grams of triethylamine in 40 mL of methylene chloride at 0° is added dropwise over 10 minutes 1.4 grams of propionyl chloride. After 1.5 hours at 0°, the reaction mixture is allowed to warm to room temperature and stirred an additional 6 hours. The mixture is made acidic with 10% aqueous hydrochloric acid and separated, and the organic layer is washed with water and brine, dried over magnesium sulfate and concentrated to leave 5.0 grams of a red syrup. Purification by silica gel chromatography using ethyl acetate:/heptane 1:20 as eluent provides 2.6 grams of 2-hydroxy-4'-phenylthio-4-propionyloxybenzophenone as a light yellow solid, melting at 88–900° C., Mass. Spec. (ci, isobutane) m/z 379 ($M^+$+1).

Analysis: Calcd, for $C_{22}H_{18}O_4S$: C, 69.8; H, 4.8; S, 8.5. Found: C, 69.9; H, 4.7; S, 8.9.

EXAMPLE 10

4-(3,5-di-tert-Butyl-4-hydroxybenzoyloxy)-2-hydroxy-4'-phenylthiobenzophenone To a stirred solution of 3.0 grams of 4'-phenylthio-2,4-dihydroxybenzophenone and 1.4 grams of triethylamine in 20 mL of toluene is added dropwise a toluene solution of 3,5-di-tert-butyl-4-hydroxybenzoyl chloride. After 3 hours at room temperature, the mixture is made acidic with 10% aqueous hydrochloric acid and extracted with ethyl acetate. The organic layer is washed with water and brine, dried over anhydrous sodium sulfate and concentrated to leave 5.5 grams of an orange paste. Purification by silica gel chromatography provides 3.2 grams of the title compound as a light yellow solid, Mass. Spec. m/z 554 ($M^+$).

EXAMPLE 11

4-Butoxy-2-hydroxy-4'-(2-hydroxyethylthio) benzophenone

Following the procedure of Example 2, the title compound is prepared by reacting equimolar amounts of 4'-chloro-2-hydroxy-4-butoxybenwphenone and 2-mercaptoethanol in the presence of potassium carbonate.

EXAMPLE 12

1,3-bis-[3-Hydroxy-4-(4-phenylthiobenzoyl)phenoxy]-2-hydroxypropane

Following the general procedure of Example 3, the title compound is prepared by reacting an equivalent amount of 4'-phenylthio-2,4-dihydroxybenzophenone and a half equivalent amount of epichlorohydrin in the presence of potassium carbonate.

EXAMPLE 13

1,3-bis-[3-Hydroxy-4-(4-phenylthiobenzoyl)phenoxy]-2-propyl Methacrylate

The title compound is prepared by reacting the alcohol compound of Example 12 with an excess amount of methacrylic acid in refluxing toluene in the presence of a catalytic amount of toluenesulfonic acid.

EXAMPLE 14

4-Glycidyloxy-2-hydroxy-4'-phenylthiobenzophenone

Following the general procedure of Example 3, the title compound is prepared by reacting equimolar amounts of 4'-phenylthio-2,4-dihydroxybenzophenone and epichlorohydrin in the presence of potassium carbonate.

EXAMPLE 15

4-(2,3-dihydroxypropoxy)-2-hydroxy-4'-phenylthiobenzophenone

The tide compound is prepared by the reaction of the compound of Example 14 with water in the presence of mineral acid in tetrahydrofuran.

EXAMPLE 16

6-[3-Hydroxy-4-(4-phenylthiobenzoyl)phenoxy] hexanoic Acid

Following the general procedure of Example 3, the tide compound is prepared by reacting equimolar amounts of 4'-phenylthio-2,4-dihydroxybenzophenone and 6-bromo-hexanoic acid in the presence of potassium carbonate.

EXAMPLE 17

2-[3-Hydroxy-4-(4-phenylthiobenzoyl)phenoxy] ethyl 6-[3-Hydroxy-4-(4-phenylthiobenzoyl)phenoxy]hexanoate The title compound is prepared by reacting equimolar amounts of the alcohol compound of Example 7 and the acid compound of Example 16 in refluxing toluene in the presence of AMBERLYST® 15 strong acid resin.

EXAMPLE 18 bis-[3-Hydroxy-4-(4-phenylthiobenzoyl) phenoxyethyl]sebacate

Following the general procedure of Example 13 or Example 17, the title compound is prepared by reacting an equivalent amount of the alcohol compound of Example 7 with a half equivalent amount of sebacic acid.

EXAMPLE 19

Hexane-1,6-diyl di{6-[3-Hydroxy-4-(4-phenylthiobenzoyl)phenoxy]hexanoate}

Following the general procedure of Example 13 or Example 17, the title compound is prepared by reacting an equivalent amount of the acid compound of Example 16 with a half equivalent amount of 1,6-hexanediol.

EXAMPLE 20

1,8-bis-{[3-Hydroxy-4-(4-phenylthiobenzoyl) phenoxy]-3,6-dioxaoctane}

Following the general procedure of Example 3, the title compound is prepared by an equivalent amount of 4'-phenylthio-2,4-dihydroxybenzophenone and a half equivalent amount of 1,2-bis(2-chloroethoxy)ethane in the presence of potassium carbonate.

EXAMPLE 21

2-[3-Hydroxy-4-(4-phenylthiobenzoyl)phenoxy] ethyl 4-Benzoyl-3-hydroxyphenoxyacetate Following the general procedure of Example 17, the title compound is prepared by reacting equimolar amounts of the alcohol compound of Example 7 and 4-benzoyl-3-hydroxyphenoxyacetic acid.

EXAMPLE 22

4'-Phenylthio-2,4-dihydroxybenzophenone

A mixture of 39 g (156 mmol) of 2,4-dihydroxy-4'-chlorobenzophenone, 22.4 g (204 mmol) of thiophenol and 26 g (188 mmol) of potassium carbonate is stirred in 300 ml of N-methyl-2-pyrrolidone for 24 hours at a temperature of 210° C. After cooling the reaction mixture is neutralized with hydrochloric acid (10%) and extracted with 4×250 ml of ethyl acetate. The solution so obtained is washed with water and afterwards with a saturated solution of sodium chloride. The residue which is obtained, after drying over anhydrous magnesium sulfate, filtration and evaporation of the solvent is subjected to chromatography on silica gel (ethyl acetate/hexane 1:5). The product is recrystallized from ethyl acetate/hexane. 21.5 g of the compound are obtained as yellow crystals with a melting point of 117–118° C.

Analysis: Calcd. for $C_{19}H_{14}O_3S$: C, 70.8; H, 4.4; S, 9.9. Found: C, 70.9; H, 4.5; S, 9.9.

EXAMPLE 23

2-Hydroxy-4-[3-tris-(trimethylsiloxy)silyl] propyloxy-4'-chlorobenzophenone

A mixture of 20 g (80 mmol) of 2,4-dihydroxy-4'-chlorobenzophenone, 59.7 g (160 mmol) of 3-chloropropyl-tris-(trimethylsiloxy)silane, 1.33 g of potassium iodide and 13.2 g of potassium carbonate is stirred in 200 ml of N,N-dimethylacetamide for 3 hours under nitrogen at a temperature of 85° C. After cooling, the mixture is concentrated in vacuum. The oily residue is subjected to chromatography (ethyl acetate/hexane 1:100). 17.5 g of the compound are obtained as a pale yellow oil.

Analysis: Calcd. for $C_2H_{41}O_6Si_4Cl$: C, 51.3; H, 7.1; Cl, 6.1. Found: C, 50.8; H, 7.3; Cl, 6.6.

EXAMPLE 24

2-Hydroxy-4-[3-tris-(trimethylsiloxy)silyl] propyloxy-4'-phenylthiobenzophenone

Using the general procedure of Example 23, but with an equivalent amount of 2,4-dihydroxy-4'-phenylthiobenzophenone in place of 2,4-dihydroxy-4'-chlorobenzophenone, the tide compound is obtained as a pale yellow oil.

Analysis: Calcd. for $C_{31}H_{46}O_6Si_4S$: C, 56.5; H, 7.0; S, 4.9. Found: C, 55.0; H, 7.4; S, 4.4.

EXAMPLE 25

2-Hydroxy-4-dodecyloxy-4'-chlorobenzophenone

A mixture of 20 g (80 mmol) of 2,4-dihydroxy-4'-chlorobenzophenone, 21.9 g (88 mmol) of 1-bromododecane and 8.4 g (100 mmol) of sodium hydrogen carbonate is heated in 77.6 g of sec-butanol and 25.6 g of water and refluxed for 20 hours. The reaction mixture is then stirred for 15 minutes in the presence of 0.8 g of active carbon and filtered while warm. The product crystallizes upon cooling. After recrystallization from sec-butanol, 21.5 g of pale yellow crystals are obtained having a melting point of 61–63° C.

Analysis: Calcd. for $C_{25}H_{33}O_3Cl$: C, 72.0; H, 7.9; Cl, 8.5. Found: C, 72.1; H, 8.1; Cl, 8.5.

EXAMPLE 26

2-Hydroxy-4-dodecyloxy-4'-phenylthiobenzophenone

Using the general procedure of Example 25, but with an equivalent amount of 2,4-dihydroxy-4'-phenylthiobenzophenone in place of 2,4-dihydroxy-4'-chlorobenzophenone, the title compound is obtained as pale yellow crystals with a melting point of 59–60° C.

Analysis: Calcd. for $C_{31}H_{38}O_3S$: C, 75.9; H, 7.8; S, 6.5. Found: C, 75.9; H, 7.8; S, 6.7.

EXAMPLE 27

Comparative UV Absorption

The following UV absorbance and molar extinction coefficient ($\epsilon$) data at four different wavelengths in the near ultraviolet illustrate the superior absorption of the instant thioether substituted benzophenones at longer wavelengths compared to the corresponding non-sulfur substituted benzophenones and to the analogous sulfonyl substituted benzophenones. The concentration of all samples in the following illustrations are 20 mg/L in ethyl acetate.

| Compound | λ325 nm | λ335 nm | λ360 nm | λ370 nm |
|---|---|---|---|---|
| | Absorbance | | | |
| UV 531* | 0.570 | 0.500 | 0.084 | 0.012 |
| Ex. 3* | 0.780 | 0.832 | 0.394 | 0.161 |
| Sulfone** | 0.460 | 0.445 | 0.169 | 0.077 |
| Ex. 2** | 0.967 | 0.997 | 0.402 | 0.148 |
| Sulfone*** | 0.250 | 0.261 | 0.121 | 0.060 |
| Ex. 10*** | 0.589 | 0.584 | 0.278 | 0.105 |
| | Molar Extinction Coefficient ($\epsilon$) | | | |
| UV 531* | 9,300 | 8,200 | 1,400 | 200 |
| Ex. 3* | 16,900 | 18,000 | 8,600 | 3,500 |
| Sulfone** | 10,300 | 9,900 | 3,800 | 1,700 |
| Ex. 2** | 20,000 | 20,700 | 8,300 | 3,100 |
| Sulfone*** | 7,300 | 7,700 | 3,500 | 1,800 |
| Ex. 10*** | 16,300 | 16,200 | 7,700 | 2,900 |

*The first pair compares the compound of Example 3 to the analogous, commercially available 2-hydroxy-4-octyloxybenzophenone (CYASORB ® UV 531, Cytec Corp.).
**The second pair compares the compound of Example 2 to the analogous 4'-sulfonyl derivative (prepared by hydrogen peroxide oxidation of Example 2). The alkyl sulfone of this illustration is similar to the substituted ethyl sulfone derivatives of U.S. Pat. No. 3,431,306.
***The third pair compares the compound of Example 10 to the analogous 4'-sulfonyl derivative. The preparation of this sulfonyl derivative is described in U.S. Pat. No. 4,029,684 and represents the closest prepared example of said patent to the compounds of the instant invention.

*The first pair compares the compound of Example 3 to the analogous, commercially available 2-hydroxy-4-octyloxybenzophenone (CYASORB® UV 531, Cytec Corp.).
**The second pair compares the compound of Example 2 to the analogous 4'-sulfonyl derivative (prepared by hydrogen peroxide oxidation of Example 2). The alkyl sulfone of this illustration is similar to the substituted ethyl sulfone derivatives of U.S. Pat. No. 3,431,306.
***The third pair compares the compound of Example 10 to the analogous 4'-sulfonyl derivative. The preparation of this sulfonyl derivative is described in U.S. Pat. No. 4,029,684 and represents the closest prepared example of said patent to the compounds of the instant invention.

It is clear from these absorbance and molar extinction coefficient data that the instant compounds each containing a thio moiety exhibit very enhanced absorption in the UV at longer wavelengths compared to a representative commercial benzophenone UV absorber and compared to the corresponding sulfonyl compounds otherwise structurally the same.

EXAMPLE 28

Light Stabilization

To demonstrate that the instant compounds with enhanced UV absorbance at the longer UV wavelengths protect epoxy E-coat primer surfaces in automotive coatings far better than presently available benzophenone Uw absorbers, the compound of Example 3 is compared against four commercially available benzophenones. The protection of the epoxy E-coat primer surface is of great importance in preventing delamination of paint-containing clearcoat films from automobiles particularly when exposed to long UV wavelengths.

Steel test panels containing a commercial epoxy primer, deposited by cathodic electrodeposition, are prepared by spray applying a 1.82.0 mil (0.036–20.051 mm) thick film of a commercially available high solids thermoset acrylic melamine clearcoat containing 3% by weight of the test UV-absorber directly over the 4"×12" (10.16 cm×30.48 cm) UNIPRIMER panels obtained from Advance Coating Technology, Inc. The coated panels are then baked at 250° F. (121° C.) for 30 minutes. After storage for one week in an air-conditioned room, the panels are exposed in Florida at 5 degrees South on a black box according to SAE J-1976. The panels are evaluated for delamination and are deemed to have failed when delamination is evident on at least 10 percent of the panel. The results of this Florida exposure are seen in the table below.

| UV Test Compound* | Time to Failure (days) |
|---|---|
| None | 13 |
| UVA1 | 87 |
| UVA 2 | 41 |
| UVA 3 | 110 |
| UVA 4 | 60 |
| Example 3 | 116** |

*UVA 1 is 2,4-dihydroxybenzophenone.
UVA 2 is 2-hydroxy-4-methoxybenzophenone.
UVA 3 is 2,2'-dihydroxy-4-methoxybenzophenone.
UVA 4 is 2-hydroxy-4-octyloxybenzophenone.
Example 3 is 2-hydroxy-4-octyloxy-4'-phenylthiobenzophenone.
**average of two panels

What is claimed is:

1. A composition stabilized against actinic induced degradation which comprises
    (a) an organic material subject to actinic induced degradation, and
    (b) an effective stabilizing amount of a compound of formula I

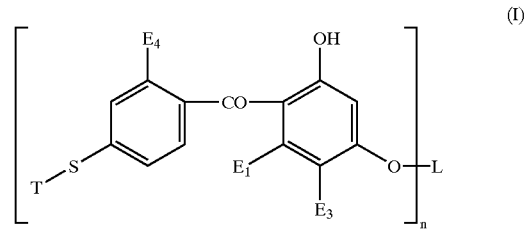

wherein
n is 1 to 4,
T is alkyl of 1 to 20 carbon atoms, alkyl of 2 to 12 carbon atoms substituted by hydroxyl, by alkoxy of 1 to 12 carbon atoms, by siloxysilyl group of formula IV, by alkanoyloxy of 2 to 12 carbon atoms, by alkenoyloxy of 3 to 12 carbon atoms or by halogen, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms,
$E_1$ is hydrogen or —$OE_2$,
$E_2$ is hydrogen or alkyl of 1 to 18 carbon atoms,
$E_3$ is hydrogen or alkyl of 1 to 8 carbon atoms,
$E_4$ is hydrogen or hydroxyl,
when n is 1, L is hydrogen, straight or branched chain alkyl of 1 to 20 carbon atoms, said alkyl substituted by alkoxycarbonyl of 2 to 20 carbon atoms, by carboxyl, by alkylcarbonyl of 2 to 20 carbon atoms, by alkenylcarbonyl of 3 to 18 carbon atoms, or by siloxysilyl group of formula IV, alkyl of 2 to 20 carbon atoms substituted by one or two hydroxyl, by alkoxy of 1 to 12 carbon atoms or by phenoxy, alkyl of 2 to 20 carbon atoms substituted by one hydroxyl and by alkoxy of 1 to 12 carbon atoms or by phenoxy, or alkyl of 2 to 20 carbon atoms substituted by alkanoyloxy of 2 to 20 carbon atoms or by alkenoyloxy of 3 to 20 carbon atoms, glycidyl, alkyl of 4 to 20 carbon atoms interrupted by one to six oxygen atoms, by one or two carbonyloxy or oxycarbonyl groups, or L is alkanoyl of 2 to 18 carbon atoms, alkenoyl of 3 to 18 carbon atoms, benzoyl, benzoyl substituted by one or two alkyl of 1 to 4 carbon atoms or a group of formula II or III

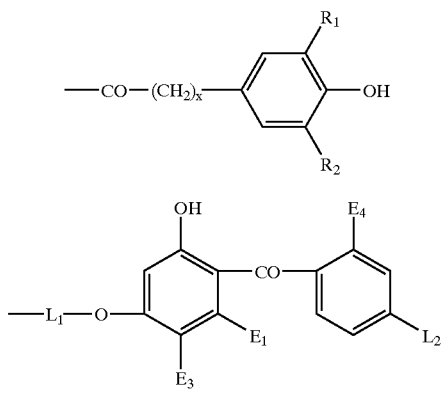

where
x is 0, 1 or 2,
$R_1$ is alkyl of 1 to 12 carbon atoms or cycloalkyl of 5 to 8 carbon atoms,
$R_2$ is sec- or tert-alkyl of 3 to 12 carbon atoms or cycloalkyl of 5 to 8 carbon atoms,
$L_1$ has the same meaning as L when n is 2,
$L_2$ is hydrogen or alkyl of 1 to 18 carbon atoms,
when n is 2, L is straight or branched chain alkylene of 1 to 12 carbon atoms, alkylene of 3 to 12 carbon atoms substituted by hydroxyl, by alkoxy of 1 to 8 carbon atoms, by alkoxycarbonyl of 2 to 20 carbon atoms, by alkanoyloxy of 2 to 20 carbon atoms, by alkenoyloxy of 3 to 20 carbon atoms or by a siloxysilyl group of formula IV, or L is alkylene of 4 to 20 carbon atoms interrupted by one or two carbonyloxy or oxycarbonyl groups, alkylene of 4 to 20 carbon atoms interrupted by one to six oxygen atoms, o-xylylene, m-xylylene, p-xylylene, isophthaloyl, phthaloyl, terephthaloyl or a,balkanedioyl of 4 to 12 carbon atoms,
when n is 3, L is straight or branched chain alkanetriyl of 3 to 12 carbon atoms, alkanetrioyl of 3 to 12 carbon atoms, trimellitoyl or alkanetriyl of 6 to 20 carbon atoms interrupted by three carbonyloxy or oxycarbonyl groups,
when n is 4, L is straight or branched chain alkanetetrayl of 4 to 16 carbon atoms, alkanetetroyl of 4 to 16 carbon atoms, pyromellitoyl or alkanetetrayl of 8 to 24 carbon atoms interrupted by four carbonyloxy or oxycarbonyl groups, and
where, when T or L is a group of formula IV,

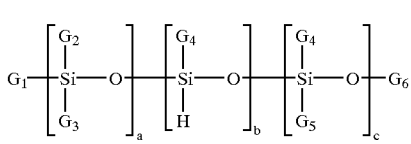

where
a is 1–50,
b is 0–50,
c is 0–50,
$G_1$ is hydroxyl, alkyl of 1 to 12 carbon atoms, alkoxy of 1 to 4 carbon atoms, cyclohexyl or —O—Si$(G_4)_3$,
$G_2$ is $G_4$ or —O—Si$(G_4)_3$,
$G_3$ is a direct bond or a bivalent group of the formula —$C_nH_{2n}$—, —$(CH_2)_nO$—, —$CH_2CH(OH)CH_2O$— or —$CH_2CH(OH)CH_2$—O—$(CH_2)_3$— where n is 1 to 4,
$G_4$ is alkyl of 1 to 12 carbon atoms, alkoxy of 1 to 4 carbon atoms, cyclohexyl or phenyl,
$G_5$ is alkyl of 1 to 18 carbon atoms, alkoxy of 1 to 4 carbon atoms, cycloalkyl of 5 to 7 carbon atoms or phenyl, and
$G_6$ is hydrogen, alkyl of 1 to 12 carbon atoms, cyclohexyl, phenyl or —Si$(G_4)_3$, or $G_1$ and $G_6$ are linked together to form a direct bond.

2. A composition according to claim 1, where in formula I, n is 1 or 2.

3. A composition according to claim 2 wherein n is 1.

4. A composition according to claim 1, where in formula I, T is alkyl of 1 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms.

5. A composition according to claim 4 wherein T is alkyl of 1 to 18 carbon atoms, allyl, cyclohexyl, phenylalkyl of 7 to 9 carbon atoms, phenyl or said phenyl substituted by one or two methyl groups.

6. A composition according to claim 5 wherein T is alkyl of 4 to 12 carbon atoms or phenyl.

7. A composition according to claim 1, where in formula I, $E_1$ is hydrogen or is —$OE_2$ where $E_2$ is hydrogen or alkyl of 1 to 12 carbon atoms; $E_3$ is hydrogen; and $E_4$ is hydrogen or hydroxyl.

8. A composition according to claim 7 wherein $E_2$ is hydrogen or alkyl of 1 to 8 carbon atoms.

9. A composition according to claim 1, where in formula I, when n is 1, L is hydrogen, alkyl of 1 to 12 carbon atoms, alkyl of 2 to 12 carbon atoms substituted by alkoxycarbonyl of 2 to 12 carbon atoms, by alkanoyloxy of 2 to 12 carbon atoms or by alkenoyloxy of 3 to 12 carbon atoms, alkyl of 2 to 4 carbon atoms substituted by hydroxyl, alkyl of 2 to carbon atoms substituted by alkoxy of 2 to 8 carbon atoms or by phenoxy, alkyl of 2 to 4 carbon atoms substituted by one hydroxyl and by alkoxy of 2 to 8 carbon atoms or phenoxy, alkanoyl of 2 to 8 carbon atoms, or L is a group of formula II where x is 0 and $R_1$ and $R_2$ are each tert-alkyl of 4 to 8 carbon atoms or a group of formula IV.

10. A composition according to claim 9 wherein, when n is 1, L is hydrogen, alkyl of 3 to 8 carbon atoms, said alkyl substituted by alkoxycarbonyl of 2 to 8 carbon atoms, by alkanoyloxy of 2 to 8 carbon atoms or by alkenoyloxy of 3 to 8 carbon atoms, or L is 2-hydroxyethyl, alkyl of 3 carbon atoms substituted by alkoxy of 2 to 8 carbon atoms or by phenoxy, alkyl of 3 carbon atoms substituted by one hydroxyl and by alkoxy of 2 to 8 carbon atoms or phenoxy, alkanoyl of 2 to 4 carbon atoms or a group of formula II where x is 0 and $R_1$ and $R_2$ are each tert-butyl.

11. A composition according to claim 1 wherein, when n is 2, L is alkylene of 3 to 12 carbon atoms, said alkylene substituted by hydroxy or interrupted by carbonyloxy or oxycarbonyl.

12. A composition according to claim 1 where in formula I, when n is 2, L is alkylene of 3 to 10 carbon atoms.

13. The composition according to claim 1 wherein component (b)is (a) 4'-phenylthio-2,4-dihydroxybenzophenone;
(b) 4-butoxy-2-hydroxy-4'-octylthiobenzophenone;
(c) 2-hydroxy-4-octyloxy-4'-phenylthiobenzophenone;
(d) ethyl 6-[3-hydroxy-4-(4-phenylthiobenzoyl)phenoxy] hexanoate;
(e) 1,6-bis-[3-hydroxy-4-(4-phenylthiobenzoyl)phenoxy] hexane;
(f) 1,10-bis-[3-hydroxy-4-(4-phenylthiobenzoyl) phenoxy]decane;
(g) 2-hydroxy-4-(2-hydroxyethyloxy)-4'-phenylthiobenzophenone;
(h) 2-hydroxy-4-(2-hydroxy-3-phenoxypropoxy)-4'-phenylthiobenzophenone;
(i) 2-hydroxy-4'-phenylthio-4-propionyloxybenzophenone;
(j) 4-(3,5-di-tert-butyl-4-hydroxybenzoyloxy)-2-hydroxy-4'-phenylthiobenzophenone;
(k) 2-hydroxy-4-(3-tris-trimethylsiloxysilyl)propyloxy-4'-phenylthiobenzophenone; or
(m) 2-hydroxy-4-dodecyloxy-4'-phenylthiobenzophenone.

14. A composition according to claim 1 wherein component (a) is a polymer selected from the group consisting of polypropylene, polyethylene, polyesters, polyvinyl chloride, polyurethanes, polyamides, polyphenylene sulfide, polyphenylene oxide, polystyrene, polyacrylates, polyacetal, polybutadiene, copolymers and blends of styrene and acrylonitrile on polybutadiene, acrylic resins with melamine cross-linking agents, acrylic alkyd or polyester resins with isocyanate cross-linking agents and epoxide resins with carboxylic acid, anhydride or amine cross-linking agents.

15. A composition according to claim 14 wherein component (a) is polyphenylene sulfide or an epoxy resin.

16. A composition according to claim 1 which additionally contains a hindered amine stabilizer wherein the N-atom is substituted by hydrogen, oxyl, hydroxyl, methyl, benzyl, hydrocarbyloxy or acyloxy.

17. A composition according to claim 1 which additionally contains another ultraviolet absorber selected from the group consisting of the benzotriazoles, benzophenones, benzoates, acrylates, organic nickel compounds, oxalamides and s-triazines.

18. A composition according to claim 16 which additionally contains another ultraviolet absorber selected from the group consisting of the benzotriazoles, benzophenones, benzoates, acrylates, organic nickel compounds, oxalamides and s-triazines.

* * * * *